United States Patent [19]

Tomalia et al.

[11] 4,112,067

[45] Sep. 5, 1978

[54] METHOD FOR TREATING POISON IVY DERMATITIS USING CERTAIN POLYAMINES AND POLYTERTIARYAMIDES

[75] Inventors: Donald A. Tomalia; Yancey J. Dickert; Leslie P. McCarty, all of Midland, Mich.

[73] Assignee: The Dow Chemical Company, Midland, Mich.

[21] Appl. No.: 769,479

[22] Filed: Feb. 17, 1977

[51] Int. Cl.$^2$ .............................................. A61K 31/74
[52] U.S. Cl. ......................................... 424/78; 424/80
[58] Field of Search .................................... 424/78, 80

[56] References Cited

U.S. PATENT DOCUMENTS

| 3,483,141 | 12/1969 | Litt et al. | 260/2 EN |
| 3,976,781 | 8/1976 | Kalopissis | 424/309 |

OTHER PUBLICATIONS

Handbook of Non-Prescription Drugs, pp. 172–175 (1923), Pub. American Pharmaceutical Association.
Kirk–Othmer, Encyclopedia of Chemical Technology, vol. 21, pp. 435–437 (1970).

*Primary Examiner*—Leonard Schenkman
*Attorney, Agent, or Firm*—James W. Ambrosius

[57] ABSTRACT

Dermatitis caused by exposure of the skin to a plant of the genus Rhus is treated and controlled by the topical application of an effective amount of a polyamine or polytertiaryamide.

8 Claims, No Drawings

METHOD FOR TREATING POISON IVY DERMATITIS USING CERTAIN POLYAMINES AND POLYTERTIARYAMIDES

BACKGROUND OF THE INVENTION

Contact with poison ivy (*Rhus toxicodendron*) or other species of the genus Rhus, which also includes poison ivy and poison sumac, will produce various degrees of dermatitis in some persons. The allergenic oil of poison ivy is a mixture of four compounds each of which has the general skeletal structure of 3-pentadecylcatechol. See. *J. Org. Chem.* 24, 980 (1959).

The bonding that takes place between various water-soluble polymers and phenols has been described. *Jour. Polymer Science* 14, 1939 (1976). However, the utility of these compounds in the treatment of poison ivy dermatitis has never been reported.

SUMMARY OF THE INVENTION

This invention relates to a method of controlling and treating dermatitis in a person who has been exposed to the antigen produced by plants of the genus Rhus comprising the topical application of an effective amount of a polyamine or polytertiaryamide. The present invention is also directed to a prophylactic method for protecting the skin against dermatitis caused by exposure to a plant of the genus Rhus which comprises topical application of an effective amount of a polyamine or polytertiaryamide to the skin prior to exposure to the plant.

The polyamine compounds used in the present method are made of recurring units which are represented by the general formula

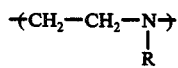   I wherein R represents hydrogen, a lower alkyl of from 1 to about 3 carbon atoms, or a substituted hydroxy lower alkyl having from 1 to about 3 carbon atoms.

Polytertiaryamides that may be used in the method of the present invention may have the nitrogen either contained in the backbone chain or contained in a side group of the carbon backbone. Thus the polytertiaryamides wherein the nitrogen is incorporated into the main backbone may be represented by the general formula

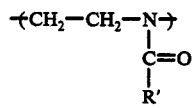   II wherein R' represents hydrogen or a lower alkyl of from 1 to about 3 carbon atoms.

Polytertiaryamides wherein the nitrogen is contained in a side group may be represented by the general formulas

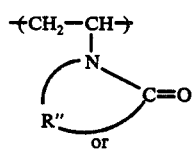   III or

-continued

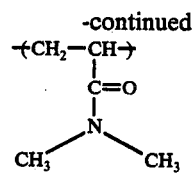   IV wherein R", the nitrogen, and the acyl group taken together represent a five or six membered heterocyclic ring wherein an atom of oxygen may optionally replace a carbon atom in the ring. Thus groups within the contemplation of the present invention would include, for example, morpholidone, oxazolidone, pyrollidone and the like.

Polymers corresponding to the formula II above wherein the acyl groups are partially hydrolyzed to an amine are also within the contemplation of the present invention. Therefore, polymers containing repeating units of both formula I and formula II may also be used in the practice of the present method. As used herein, the term "an effective amount" refers to the amount of polyamine or polytertiaryamide sufficient to cause a significant decrease in the severity of the dermatitis or sufficient to prevent or delay the development of the dermatitis.

Polymers of the type used in the practice of the method of the invention generally have a molecular weight in excess of 5000.

In practicing the method of the invention, the compound is applied topically to the skin where exposure to the antigen occurred or is expected to occur. The polymer may be applied following exposure to prevent or control the development of dermatitis, or the polymer may be applied after the dermatitis has developed to prevent further spread of the dermatitis and to soothe the existing irritation. The active compound is generally applied to the skin as a composition in combination with a carrier in suitable form for topical application. Such a composition may be in the form of a solution, suspension, or emulsion. In general, an aqueous solution of the active polymer is preferred. Such compositions may contain additional active ingredients, excipients, perfumes, thickeners, stabilizers, or the like. Methods for preparing compositions used in the invention are well known to those skilled in the art. The preparation of solutions and suspensions are discussed in Remington's Pharmaceutical Sciences 13th Ed. (Mack Publishing Co., 1965). In general, aqueous solutions containing about 1% to 50% polymer solids may be used. Higher polymer concentrations are also operable but are less esthetically pleasing above the given range.

DETAILED DESCRIPTION OF THE INVENTION

The following examples will serve to further illustrate the present invention but are not to be construed as limitations thereon.

EXAMPLE 1

A 20 percent aqueous solution of poly[((1-oxopropyl)imino)-1,2-ethanediyl] (molecular weight 370,000) was prepared and tested for efficacy in the treatment of poison ivy dermatitis as compared to Ziradryl® (Parke-Davis) a commercially available cream for the treatment of poison ivy dermatitis containing zirconium oxide and dephenhydramine Hcl and to no treatment.

Four human subjects were patch tested for dermatitis induced by (a) poison ivy antigen alone, (b) the antigen applied to the skin pretreated with the aqueous active polymer prepared above, and (c) the antigen applied to skin pretreated with Ziradryl ®.

Examination of the dermatitis that developed indicated that the efficacy of the active polymer and Ziradryl ® are approximately equal. Both Ziradryl ® and the active polymer caused a lag in the development of the dermatitis as compared to the untreated control exposures. The pretreated exposure areas showed a less severe inflamation of the skin than the untreated controls.

In addition, general safety studies of the active polymer indicates the use of the compound in the treatment of dermatitis will result in no unreasonable risks to a human being. The median lethal dose when given orally to rats is greater than 5 grams per kilogram of bodyweight. A 40 percent aqueous solution was found to be practically non-irritating to the skin and was found not to be a skin sensitizer.

The preparation of the active polymer, poly[((1-oxo-propyl)imino)-1,2-ethanediyl] is known to the art and described in U.S. Pat. No. 3,483,141. This compound and related polytertiaryamides of formula II above may be partially hydrolyzed by an acid or base to yield secondary amines along the backbone interspersed with the acyl groups. As noted above, such hydrolyzed derivatives are within the scope of the present invention. In general, polytertiaryamides of formula II above have a preferred molecular weight range of from about 200,000 to 600,000, although higher or lower molecular weights are also operable with the invention.

EXAMPLE 2

Polyethyleneimine (molecular weight 40–60 × $10^3$) was reacted with an equal weight of ethylene oxide to yield poly(ethyleneimine-ethylene oxide) having a molecular weight of about 80–120 × $10^3$ wherein the primary and secondary amino groups were converted to tertiary amines.

Using seven human subjects and the same procedure as given in Example 1 above, a 5 percent aqueous solution of the active polymer, was compared to Ziradryl ®, and a control. The active polymer was found to delay the development of poison ivy dermatitis as compared to the control, but was found to be generally less effective than Ziradryl ® in controlling the antigen reaction.

The active polymer was also tested for safety for use on humans, and it was found that topical application of the polymer resulted in no unreasonable risks.

While other compounds of the general formulas I, II, III, and IV were not actually tested on human subjects they also will complex with phenols related to the active antigen and would be useful in the method of the present invention. The following polymers have been shown to bind with phenolics related to the active oils present in the genus Rhus:
polyvinylpyrollidone
poly N,N-dimethylacylamide
polyvinyloxazolidone
polyvinylmorpholidones

We claim:

1. A method of treating and controlling dermatitis in humans caused by the exposure of the skin to a plant of the genus Rhus which comprises the topical application of an effective dermatitis alleviating amount of a polymer having a molecular weight of at least 5000 wherein said polymer is a polyamine of recurring units represented by the formula

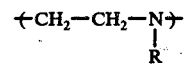

wherein R represents hydrogen, a lower alkyl of from 1 to about 3 carbon atoms, or a substituted hydroxyl lower alkyl having from 1 to about 3 carbon atoms; a polytertiaryamide of recurring units represented by the formula

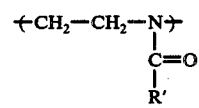

wherein R' represents hydrogen or a lower alkyl of from 1 to about 3 carbon atoms; or a partially hydrolyzed polytertiaryamide prepared from a polytertiaryamide of the formula given above.

2. The method of claim 1 wherein the polymer is a polytertiaryamide or its partially hydrolyzed product.

3. The method of claim 1 wherein the polymer is a polyamine.

4. The method of claim 3 wherein the polymer is a poly(ethyleneimine-ethylene oxide).

5. The method of claim 2 wherein R' is ethyl.

6. The method of claim 1 wherein the polymer is applied in combination with a carrier.

7. The method of claim 6 wherein the carrier is water.

8. The method of claim 1 wherein the polymer is applied prior to exposure to the plant of the genus Rhus.

* * * * *